(12) United States Patent
Memic et al.

(10) Patent No.: US 10,669,514 B1
(45) Date of Patent: Jun. 2, 2020

(54) CELL BLOCKER INSERTS FOR MULTIWELL TISSUE CULTURE PLATES

(71) Applicant: King Abdulaziz University, Jeddah (SA)

(72) Inventors: Adnan Memic, Macomb, MI (US); Tuerdimaimaiti Abudula, Jeddah (SA); Kalamegam Gauthaman, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/689,224

(22) Filed: Nov. 20, 2019

(51) Int. Cl.
*C12M 1/12* (2006.01)
*C12Q 1/02* (2006.01)

(52) U.S. Cl.
CPC ............ *C12M 23/06* (2013.01); *C12M 25/14* (2013.01); *C12Q 1/025* (2013.01)

(58) Field of Classification Search
CPC ............ B01L 3/50851; B01L 3/50853; B01L 2200/142; B01L 2300/042; B01L 2300/0829
See application file for complete search history.

(56) References Cited

U.S. PATENT DOCUMENTS

| | | | |
|---|---|---|---|
| 6,309,818 B1 | 10/2001 | Malinda et al. | |
| 6,312,886 B1 * | 11/2001 | Lee et al. ............ | B01L 3/50851 237/1 R |
| 9,533,301 B2 | 1/2017 | Yue et al. | |
| 2004/0009583 A1 * | 1/2004 | Benn et al. ......... | B01L 3/50851 435/287.2 |
| 2014/0243243 A1 | 8/2014 | Tran | |

OTHER PUBLICATIONS

Ottoson et al: "Accelerated Wound Closure—Differently Organized Nanofibers Affect Cell Migration and Hence the Closure of Artificial Wounds in a Cell Based In Vitro Model", PLOS ONE, https://doi.org/10.1371/journal.pone.0169419, Jan. 6, 2017.

* cited by examiner

*Primary Examiner* — Gautam Prakash
(74) *Attorney, Agent, or Firm* — W & C IP (57) ABSTRACT

Inserts for the wells of tissue culture plates are provided. When placed in a tissue culture well, a bottom surface of a shaft portion of an insert contacts a bottom surface of the well and blocks the growth of cells in that area. The blocked area mimics a "wound" in the layer of cells that grows around it. A cover portion of the insert comprises open channels through which cells, media, etc. can be delivered and gases exchanged while the insert is in place. Once the insert is removed, cell culture with the artificial "wound" is used to test the efficacy of agents with respect to their ability to facilitate cell growth into and closure of the "wound".

16 Claims, 9 Drawing Sheets

CELL BLOCKER INSERTS FOR MULTIWELL TISSUE CULTURE PLATES

BACKGROUND OF THE INVENTION

Field of the Invention

The invention generally relates to inserts for the wells of tissue culture plates. In particular, the invention provides inserts which, when placed in a tissue culture well, block the growth of cells in an area of the well, the blocked area mimicking a "wound" which is useful for assessing the impact of test compounds and conditions on wound healing in vitro.

Description of Related Art

There are three phases associated with the process of wound healing, including the inflammatory phase, the proliferative phase, and the remodeling phase. During the inflammatory phase, bacteria and debris are removed and macrophages release growth factors to stimulate angiogenesis and the production of fibroblasts. During the proliferative phase, granulation tissue forms and epithelialization begins, which involves migration of epithelial cells to seal the wound; fibroblasts proliferate and synthesize collagen to fill the wound and provide a strong matrix on which epithelial cells grow; and contractile cells called myofibroblasts appear in the wound and aid in wound closure. During the remodeling phase, collagen associated with scar formation undergoes repeated degradation and resynthesis, wherein the tensile strength of the newly formed skin increases. During acute inflammation, resident and recruited cells alike produce pro-inflammatory mediators including pro-inflammatory eicosanoids and pro-inflammatory cytokines. The COX and LOX enzymatic pathways, respectively, may produce pro-inflammatory eicosanoids and leukotrienes, but also are necessary for production of lipid mediators involved in programmed resolution, namely eicosanoid mediators of lipid mediator class switching (in the case of COX), and pro-resolving metabolites in the case of LOX). All of these phases and pathways are targets for pharmaceutical drugs for the treatment of wounds, e.g. to facilitate wound closure, to control or reduce inflammation, and to prevent the formation of scar tissue and/or improve the quality (e.g. flexibility and appearance) of tissue that grows to fill the wound.

The use of animal models to test the impact of agents on wound healing is expensive, time consuming and is coming into disfavor for ethical reasons. It would be of great benefit to have available reliable methods to create "artificial" or "simulated" wounds, e.g. in cell culture, to rapidly assess the impact of various agents on wound healing in a cost-effective manner.

While scratch assays are currently used to study cell migration and cell-cell interaction with respect to wound healing, they are done by making a scratch on a cell monolayer to simulate a wound and capturing images of cell behavior at regular intervals by time lapse microscope. However, scratch assays are not adaptable for cells that are grown in three-dimensions, e.g. on a scaffold.

SUMMARY OF THE INVENTION

The disclosure provides inserts for the wells of tissue culture plates and methods of using the inserts during tissue culture to mimic or simulate a wound (i.e. to create an artificial "wound") in cultured cells. The inserts are especially useful to simulate wounds in a culture of cells grown on a 3-dimensional scaffold or sheet material. Cells grown in tissue culture perceive or interpret a gap, space or void in the culture as a wound. When placed in a tissue culture well, a bottom surface of a shaft portion of an insert as disclosed herein extends to the bottom surface of the well and blocks the growth of cells in an area that is predefined by the shape and size of the bottom surface of the shaft, thereby creating a gap in the cell layer or cell mass. In some aspects, a scaffolding material is present in the bottom of the well and the insert extends to (or even into) the material, pressing it against the bottom of the well, holding it in place and preventing growing cells from entering the space occupied by the shaft. The blocked area thus mimics a "wound" in the layer(s) of cells growing on and in the scaffold. A cover portion of the insert comprises open channels through which cells, media, air, etc. are delivered or exchanged while the insert is in place. Once the insert is removed, the cultured cells with the artificial "wound" are used, e.g. to test agents for their ability to facilitate cell proliferation and migration into the gap, simulating closure of a "wound".

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide an insert to prevent cell growth in a predetermined area of a cell culture well, comprising i) a cover portion comprising a top surface and a bottom surface, wherein the cover portion extends between the top surface and the bottom surface, and comprises a flanged top section and a cylindrical bottom section contiguous with the flanged top portion; and at least one channel extending between the top surface and the bottom surface; and ii) a shaft portion having sides that extend from the bottom surface to a shaft bottom surface that is substantially planar; wherein the shaft portion has a cross-sectional area that is less than a cross-sectional area of the cylindrical bottom section. In some aspects, the cover portion and the shaft portion are molded as a single piece. In other aspects, the insert is sized for use in a 96 well culture plate, a 48 well culture plate, a 24 well culture plate, a 12 well culture plate or a 6 well culture plate. In further aspects, a bottom surface of the cylindrical bottom section has a diameter of: for a 96-well plate, less than 6.394 mm; for a 48-well plate, less than 11.0556 mm, for a 24-well plate, less than 16.15.62 mm; for a 12-well plate, less than 22.73 11 mm; and for a 6-well plate, less than 35.4334.8 mm. In yet further aspects, a shape of the shaft bottom surface is circular, ovoid, rectangular, linear or irregular. In some aspects, the shaft portion is substantially cylindrical.

The disclosure also provides a method of creating an artificial wound in cells in culture, comprising securing a scaffold material against a bottom surface of a cell culture well by placing the insert of claim 1 into the cell culture well, wherein the shaft bottom surface of the shaft contacts the scaffold material and holds the scaffold material against a bottom surface of the cell culture well; introducing cells and culture medium into the cell culture well via the one or more channels in the top portion of the insert, and incubating the cells under conditions that permit cell growth on the scaffold material; wherein cells grow in a non-occluded area of the scaffold material that is not contacted by the shaft bottom surface, and cells do not grow in an occluded area of the scaffold material that is contacted by the shaft bottom surface, and wherein the occluded area forms an artificial wound. In some aspects, the scaffold material comprises a polymer. In other aspects, the scaffold material comprises one or more agents that affect or may affect wound healing.

Also provided is a method of testing at least one agent for its ability to facilitate wound healing, comprising: creating an artificial wound in cultured cells by the method of claim 10, removing the insert from the cell culture well; incubating the cultured cells under conditions that permit cell growth; and assessing growth of the cultured cells; wherein if the cultured cells grow into the artificial wound at a rate that is greater than that at which cells grow into a control artificial wound, then the at least one agent facilitates wound healing. In some aspects, the control artificial wound is established by incubating cells in a control cell culture well in the absence of the at least one agent. In other aspects, the step of assessing includes measuring one or more of cell migration, speed, persistence and polarity. In further aspects, the at least one agent is or is comprised in the scaffold material.

DETAILED DESCRIPTION

External and internal wounds (such as abrasions, scratches, incisions, cuts, punctures, lacerations, etc.) typically result in cutting, sundering or removing connected cells away from each other, leaving a gap in affected tissue. In order to heal a wound, new cells must grow and cells at the wound edge must migrate into the wound space to fill the gap and/or replace cells that were removed or which died as a result of the wound. The disclosure provides inserts for the wells of cell culture dishes, e.g. multiwell plates, which create artificial wounds to study this process. Placement of the inserts into wells during cell growth blocks an area of the bottom surface of the well, and/or an area of a scaffolding that is present at the bottom of the well, thereby preventing cells from growing across the entire well surface or scaffold. This results in a gap or void space in the culture. In other words, physical exclusion creates cell-free areas by preventing cell growth in a region predefined by the size and shape of the insert. Upon removal of the insert, the gap mimics a wound which the surrounding cells attempt to "heal" by growing and migrating into the gap. Before and during the healing process, the cells are contacted with agents and/or subject to conditions to determine the effects of the agents/conditions on e.g. speed, persistence, polarity, etc. of the cells. Use of the inserts thus facilitates the testing of agents and conditions to determine which are favorable and which are unfavorable to the process of wound healing. In addition, the use of these cell blocking inserts advantageously standardizes in-vitro artificial wound healing models in terms of the size and shape of the artificial wound.

The Inserts

Figure 1:
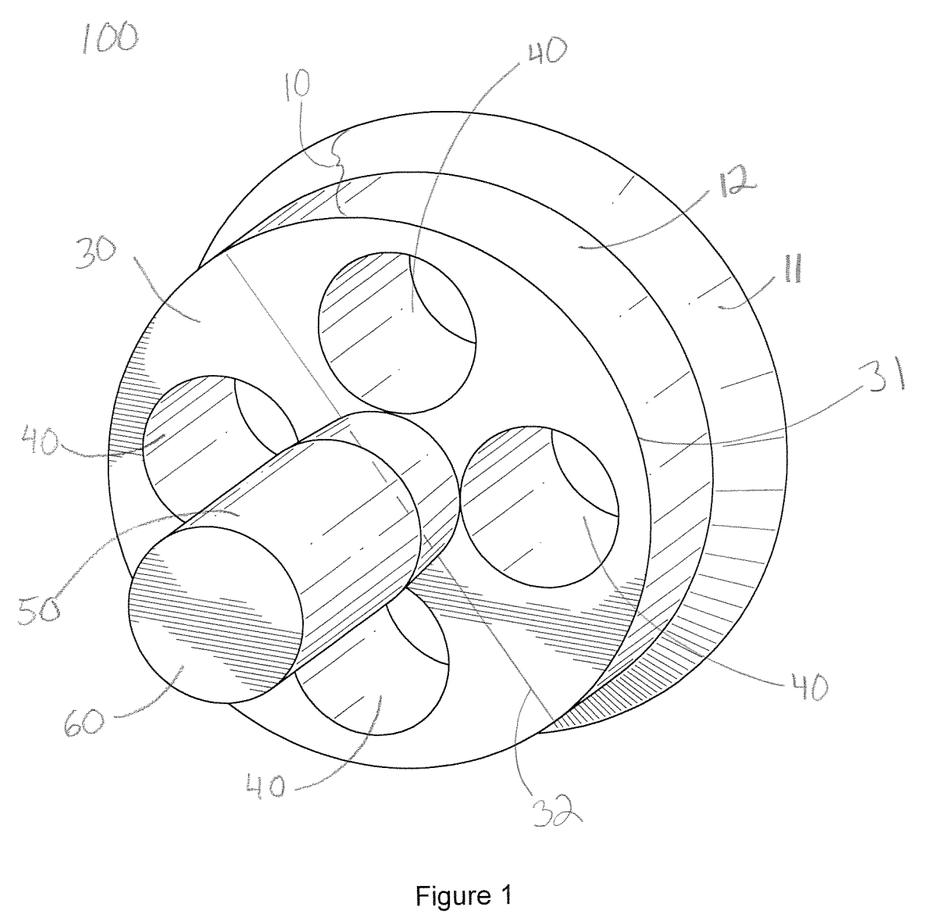
FIG. 1. Schematic illustration of the insert: a bottom perspective view.
Figure 2:
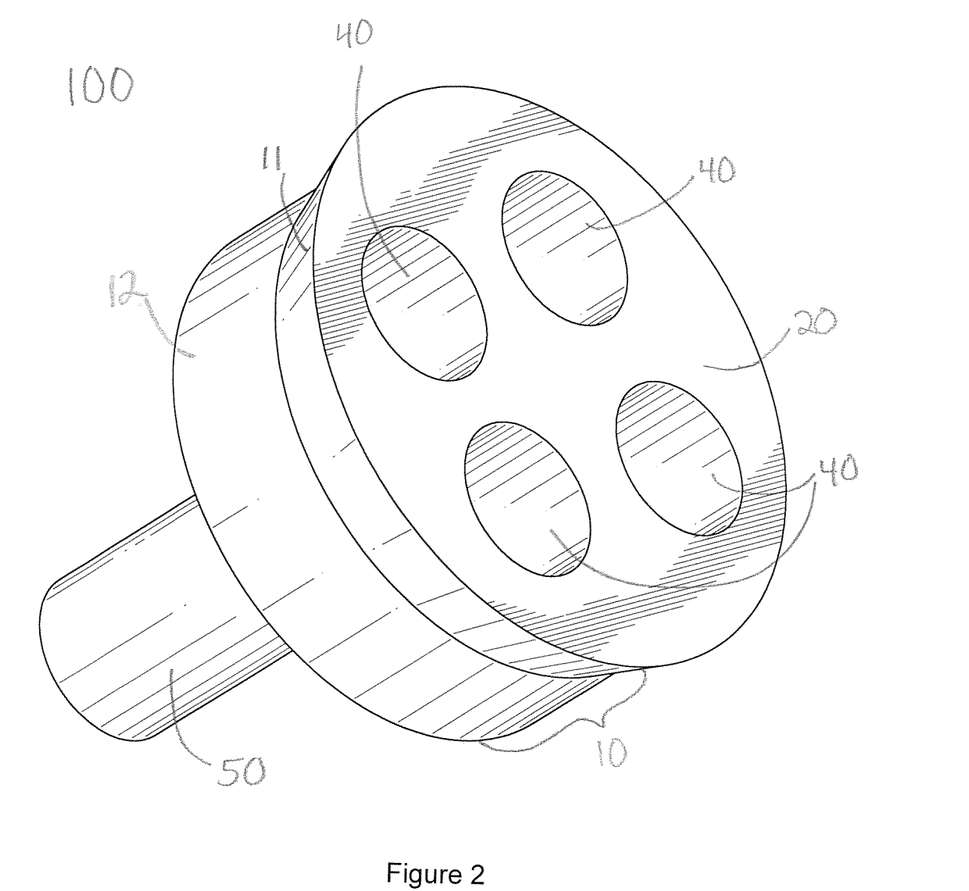
FIG. 2. Schematic illustration of the insert: a top perspective view.
Figure 5A:
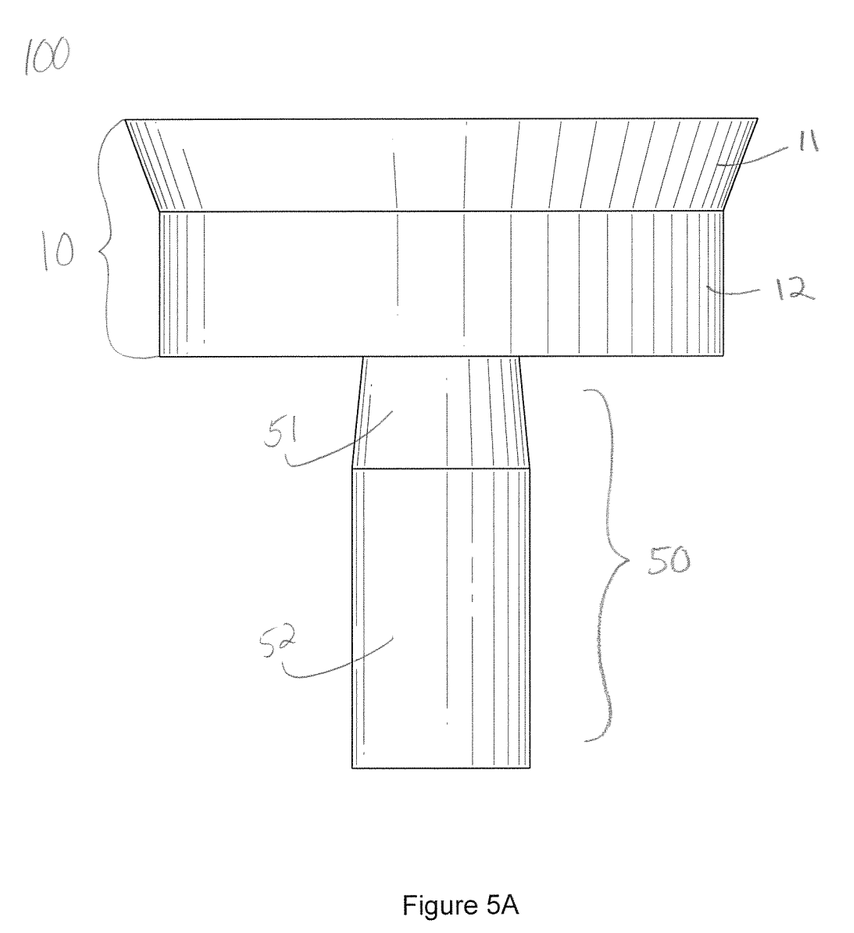
FIGS. 5A and B. Schematic illustration of the insert: A, a side view; B a top view.

FIGS. 1 and 2 show schematic views of an insert of the disclosure. With reference to FIG. 2, insert 100 comprises cover portion 10 (see also FIG. 5A) which comprises top surface 20 and bottom surface 30 (shown in FIG. 1). Cover portion 10 comprises two differently shaped sections: flanged top section 11 and cylindrical bottom section 12. The sides of flanged top section 11 are tapered at an angle and flare out from cylindrical bottom section 12, so as to form a projecting rim or collar at the top of the insert.

Figure 3A:
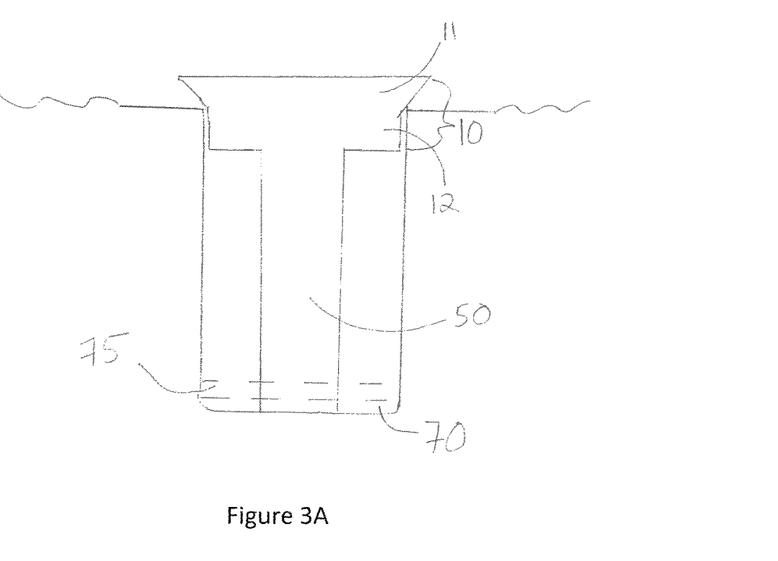
FIGS. 3A and B. Schematic illustration of the insert positioned in the well of a cell culture plate. A, insert comprising flanged upper section; B, insert without flanged upper section.

The circumference of top surface 20 is greater than a circumference of the opening of the well in which the insert is being used. Thus, when the insert is placed in a well, top section 11 does not enter, or does not completely enter, the well but protrudes at least somewhat from the surface of the cell culture plate, as shown in FIG. 3A, which shows a cross-sectional side view of an insert in a well. In contrast, cylindrical bottom section 12 is substantially cylindrical and fits snugly into the well of a cell culture plate, its circumference being slightly less than that of the well e.g. about 0.1-0.5 mm less. By protruding slightly above the surface of the cell culture plate, top portion 11 permits easy insertion and removal of the insert from a well.

As shown in FIGS. 1 and 2, at least one channel 40 extends through cover portion 10 between top surface 20 and bottom surface 30, i.e. extends completely through top section 11 and bottom section 12. FIGS. 1 and 2 show four channel 40s. However, fewer or more channels may be present, for example, from about 1 to 10 channels, such as 1, 2, 3, 4, 5, 6, 7, 8, 9 or 10 channels may be present, depending on the size of the insert and the usefulness of having a particular number of channels. In addition, FIGS. 1 and 2 show the channels as perpendicular to the sides of bottom section 12. However, this is not always the case, as one or more of the channels may also be slanted i.e. at an angle, or even irregular in shape, as long as they extend completely through the cover portion and are open at both top surface 20 and bottom surface 30. The opening of a channel 40 at top surface 20 serves as a port via which materials can be introduced into or removed from the well (exchanged) when the insert is present, e.g. solutions comprising cells, media and nutrients for cell growth, agents for testing (e.g. compounds which are begin investigated for their ability to affect cell growth), air, $CO_2$, etc.

Insert 100 also comprises shaft 50 having sides that extend from bottom surface 30 to shaft bottom surface 60. Shaft 50 extends from and/or encompasses a center of bottom surface 30 and is surrounded or flanked, at bottom surface 30, by at least one channel 40. Shaft bottom surface 60 is substantially planar and its surface area is less than the surface area of bottom surface 30, and is also less than the surface area of the well into which the insert is placed.

Figure 5B:
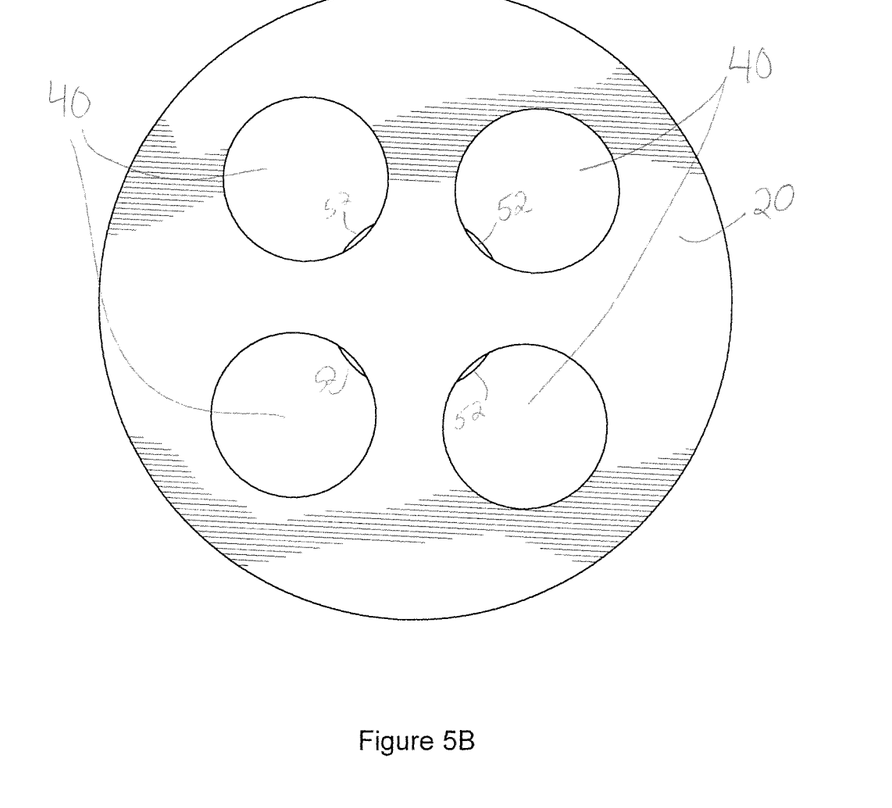

In some aspects, shaft 50 is substantially cylindrical. However in other aspects, illustrated in FIG. 5A, upper section 51 of shaft 50 is tapered at an angle away from lower section 52 of shaft 50. This design can be useful, e.g. to afford increased space for the placement of wider or more channels through cover piece 10. FIG. 5B shows a top view of this aspect, showing that, when looking straight down at top surface 20, a small portion of the sides of lower section 52 is visible in when looking through each channel.

Figure 4:
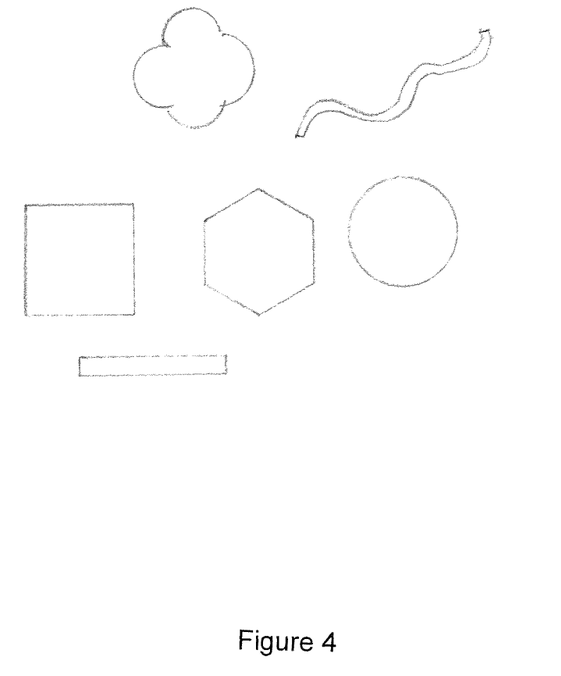
FIG. 4. Examples of shapes of the bottom of the shaft of the insert.

FIG. 1 shows shaft bottom surface 60 as circular. However, this is not always the case. As shown in FIG. 4, the shape of shaft bottom surface 60 may be rectangular, linear, irregular, etc. and its surface area may vary, depending on the type and size of artificial wound that is desired. However, the total surface area of shaft bottom surface 60 is generally less than that of bottom surface 30. In addition, the shape may or may not be uniform over the entire length of the shaft.

As discussed above, FIG. 3A shows a schematic view of an insert removably inserted into a well of a cell culture dish. As can be seen, the opening of the well is completely covered (occluded) by the top section 11 of the insert and the bottom of shaft 50 rests against the bottom of the well or, optionally, on a coating or substrate 70 that has been pre-applied to the bottom and/or sides of the well. The underlying substrate 70 and the associated extracellular matrix (ECM) are important considerations in the wound healing assays, since some cell types can grow directly on plastic or glass substrates, while others require a coating of extracellular matrix components such as gelatin, collagen, or fibronectin in order to adhere. Further, the ECM can also participate in signaling involved in cell migration. In addition, the stiffness of the underlying substrate can also modulate the dynamics of migration into the gap.

In other aspects, shaft 50 is positioned directly on a top surface of and presses down on scaffold 75, which is e.g. an optional polymeric substrate material present at the bottom of the well. In this aspect, shaft 50 serves to hold scaffold 75 in place, e.g. to prevent it from floating or moving during cell culture, as well as to exclude cells from the blocked area.

When scaffold 75 is present, cells are generally introduced onto a top surface of scaffold 75 and grow there and/or infiltrate the scaffold. Scaffold 75, which is generally comprised of fibers, facilitates cell growth mechanically e.g. by the shape and size of the fibers which make up the material, assisting the cells in 3-dimensional growth; and/or chemically, e.g. by inclusion of agents known to facilitate cell growth, as part of the fiber composition, and/or as a coating on the fibers. The materials may be woven or non-woven and may form a mesh. The fibers are generally nanoscale (less than 1000 nanometers) and/or microscale (less than 50 microns) polymer fibers and are typically fabricated by electrospinning or a similar known process. The orientation of the polymer fibers relative to one another may be regular (e.g. parallel), random, or both. The polymer fibers may include resorbable materials that further include, for example, polycaprolactone (PCL), polylactic acid (PLA), polyglycolic acid (PGA), and/or combinations thereof. The polymer fibers may also include non-resorbable materials such as polyethylene terephthalate (PET), polyetherketoneketone (PEKK), polyurethane (PU), polycarbonate (PC), polyamide (Nylon), polyglycerol sebacate (PGS) or combinations thereof. The polymer fibers may also include natural polymers comprising e.g. collagen, gelatin, fibronectin, hyaluronic acid, silk, heparin, aloe vera, lignin, chitin, chitosan and/or combinations thereof.

Preferred scaffolding material which is used in the practice of the present methods includes but is not limited to: PCL with PGS, methacrylated gelatin, core (gelatin) and shell (PCL) fibrous scaffolds, etc.

Figure 6A:
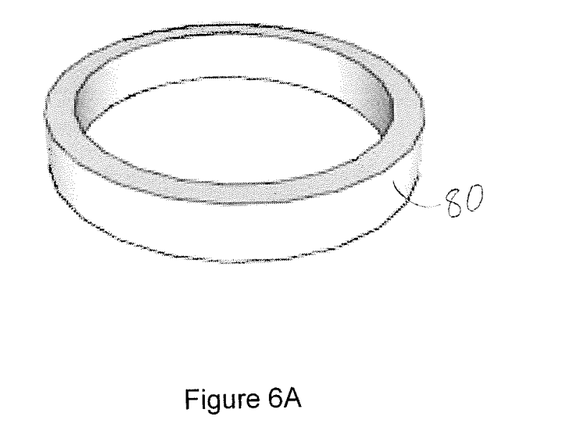
FIGS. 6A and B. A, scaffolding ring; B, insert and scaffolding ring as they would be positioned together in the well of a cell culture plate.
Figure 6B:
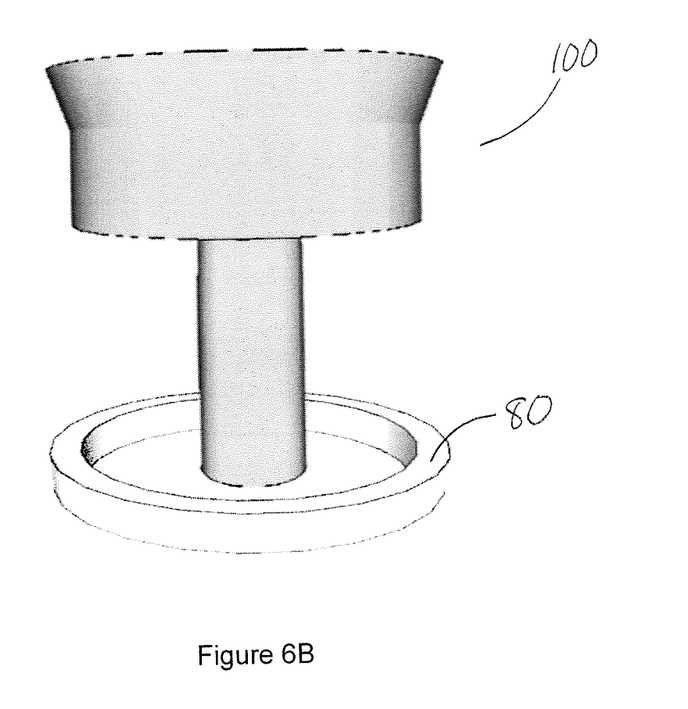

In some aspects, when a scaffold is present, the inserts are used together with scaffold ring 80, as shown in FIG. 6A. Scaffold ring 80 rests on top of scaffold 70 and against the walls of the well. The ring stabilizes the position of scaffold 70 but is of a size that does not extensively block the top surface of scaffold 70. The outer circumference of scaffold ring 80 is generally slightly less than that of the circumference of the well itself. Those of skill in the art will recognize that the size and dimensions of the ring can be adapted to accord with the dimensions of the well, as described below. FIG. 6B shows scaffold ring 80 positioned for use with insert 100.

Figure 7A:
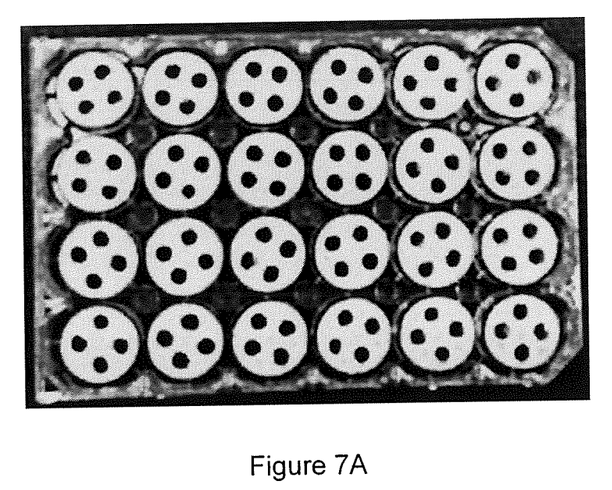
FIGS. 7A and B. The inserts positioned in a 24 well plate. A, top view; B, bottom view.
Figure 7B:
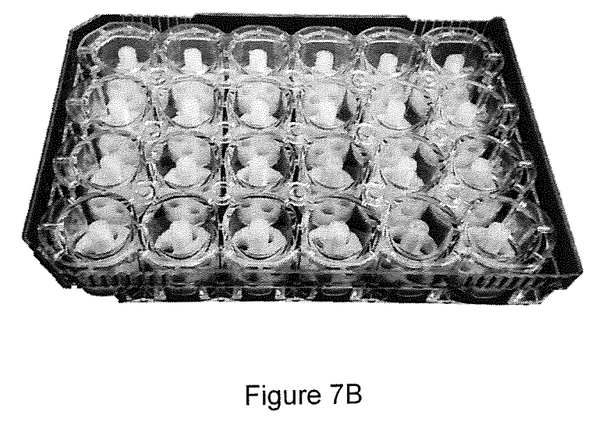
Figure 8A:
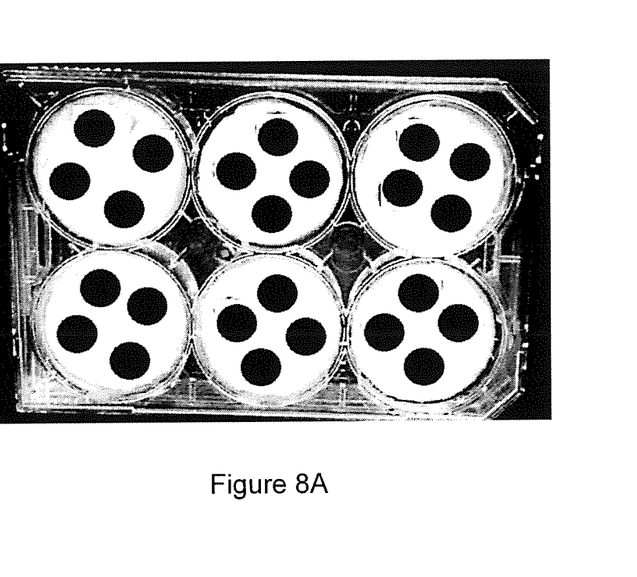
FIGS. 8A and B. The inserts positioned in a 6 well plate. A, top view; B, bottom view.
Figure 8B:
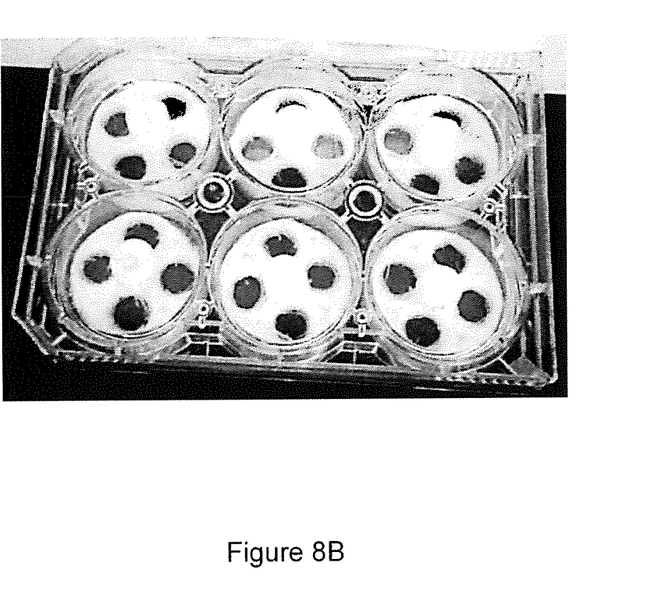

FIG. 7A shows a top view of a 24-well plate with inserts present in each well; FIG. 7B shows a bottom view of a 24-well plate with inserts present in each well 6. FIGS. 8A and 8B show similar views of a 6-well plate.

Dimensions

Figure 3B:
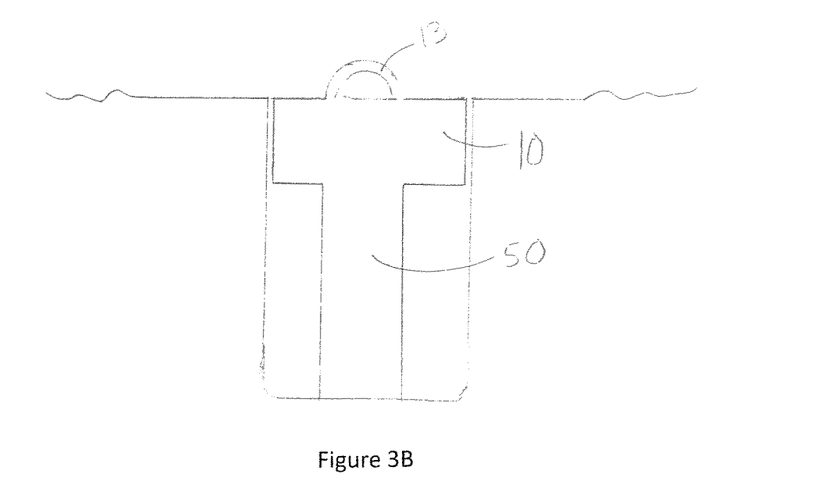

The inserts and components thereof can be of any useful size. Typically, they are sized for use in a 6, 12, 24, 48 or 96 well culture plates. Thus, with respect to FIG. 1 and FIG. 3A, in some aspects, the circumference of bottom section 12 of cover portion 10 is such that the insert fits very closely but removably into a cell culture well, the flanged top section 11 of cover portion 10 is of a larger size that bottom section 12 so that the insert cannot drop entirely into the well; the length of shaft 50 is adjusted to reach the bottom of the well when the insert is in place, and the footprint of the base of 50 shaft is sized to make a wound of a desired size. However, in other aspects, as shown in FIG. 3B, cover portion 10 is designed so that the insert can drop entirely into the well. In such aspects, cover portion 10 does not include a flanged portion 11 but may be e.g. completely cylindrical. In such aspects, cover portion 10 may optionally include an alternative means of removal, e.g. a small protruding "handle", shown as 13 in FIG. 3B, etc.

By "cross-sectional area" we mean the area of a two-dimensional shape that is obtained when a three-dimensional object—such as a cylinder—is sliced perpendicular to some specified axis at a point, generally its longest axis. For example, for a cylinder, the cross-sectional area is equal to the area of a circle if cut parallel to the circular base.

As discussed above and shown in FIGS. 1 and 2, in some aspects, cover portion 10 of the insert is made up of two contiguous, adjoining sections: a flanged top section 11 and a cylindrical bottom section 12. As shown e.g. in FIG. 2, top section 11 is of a larger size than bottom section 12 to prevent the insert from going entirely into the well. Accordingly, the area of top surface 20 of top section 11 (see FIG. 2), not including the area of the channels, is: from about 0.38 to 0.44 $cm^2$, such as about 0.427 $cm^2$ for a 96 well plate; from about 1.22 to 1.33 $cm^2$, such as about 1.278 $cm^2$ for the 48 well plate; from about 2 to about 2.63 $cm^2$, such as about 2.57 $cm^2$ for a 24 well plate; about 4.04 to about 6.16 $cm^2$, such as about 5.16 cm2 for a 12 well plate; and from about 9.5 to about 14.5 $cm^2$, such as about 12.8 $cm^2$ for the 6 well plate, depending on the overall size of the insert.

As shown in FIG. 1, smaller cylindrical bottom section 12 comprises bottom surface 30. Bottom surface 30 has a diameter 32 and circumference 31 that are sized so as to permit bottom section 12 to be placed within a well of a multi-well cell culture plate. The diameter 32 of bottom surface 30 for is thus, for example:

For a 6-well plate, less than 35.4334.80 mm, such as from about 34.43 mm to about 34.78 mm;

For a 12-well plate, less than 22.1173 mm, such as from about 21.73 mm to about 22.1 mm;

For a 24-well plate, less than 15.60 16.26 mm, such as from about 15.26 mm to about 15.562 mm;

For a 48-well plate, less than 11.0556 mm, such as from about 10.56 mm to about 11.05 mm;

For a 96-well plate, less than 6.4 mm, such as from about 5.4 mm to about 6.2 mm. These diameters correspond to an area (not including the area of the channels, or the area where shaft 60 connects to bottom surface 30) for bottom surface 30 of:

For a 6-well plate, less than about 9.58 cm²;
For a 12-well plate, less than about 4.013.83 cm²;
For a 24-well plate, less than about 1.932.08 cm²;
For a 48-well plate, less than about 0.951.05 cm²;
And for a 96-well plate, less than about 0.2932 cm².

It is noted that the area of bottom surface 30, excluding the area of the channels and the area where shaft 60 connects to bottom surface 30, corresponds to the cross-sectional area of bottom section 12, which is typically cylindrical.

The cross-sectional area of the channels ranges depending e.g. on the number of channels that are present and the overall size of the insert. Generally, a channel has a cross-sectional area ranging from about 0.01 to about 0.035 cm², such as about 0.0314 cm² for a 96 well plate; from about 0.01 to about 0.11 cm², such as about 0.095 cm² for a 48 well plate; from about 0.01 to about 0.2 cm², such as about 0.192 cm² for a 24 well plate; from about 0.01 to about 0.4 cm², such as about 0.288 cm² for a 12 well plate; and from about 0.01 to about 0.95 cm², such as about 0.72 cm² for a 6 well plate.

Shaft bottom surface 60 generally has a cross-sectional area of: from about 0.01 to about 0.15 cm², such as about 0.032 cm² for a 96 well plate; from about 0.01 to about 0.5 cm², such as about 0.099 cm² for a 48 well plate; from about 0.01 to about 1 cm², such as about 0.198 cm² for a 24 well plate; from about 0.01 to about 2 cm², such as about 0.312 cm² for a 12 well plate; and from about 0.01 to about 0.5 cm², such as about 0.78 cm² for a 6 well plate.

The height of shaft (50 mm) plus cover portion (10 mm) is generally sufficient to place the bottom surface of the shaft at the bottom of the well when the well is in use. However, if a scaffolding fabric is also placed in the bottom of the well, the combined height may be somewhat less, e.g. from 0.1-5 mm, less to leave room for the scaffold. Those of skill in the art will recognize that the scaffold can be extremely thin, e.g. "paper-thin" and have little or no impact on the height. To achieve this, the depth of cover portion 10, e.g. the distance from top surface 20 to bottom surface 30, is generally in the range of from about 14.5 mm to about 18.5 mm, such as about 18.1 mm; and the height of shaft 50 e.g. the distance from bottom surface 30 to the base of the shaft is generally in the range of from about 10 mm to about 18.5 mm, such as about 12.95 mm Those of skill in the art will recognize that the height (or depth) of multiwell plates is generally consistent across differently sized wells, being generally about 17.4 mm.

The depth of a scaffold ring is about 2-5 mm. The thickness can be about 1-3 mm. The diameter varies, depending on the size of the well in which it is used and generally approximates or is that same as that of the cylindrical bottom section, e.g. is: from about 5.8 to 6.3 mm, such as about 6.1 mm for a 96 well plate; from about 10.3 to 10.9 mm, such as about 10.5 mm for the 48 well plate; from about 15 to about 15.5, such as about 15.1 mm for a 24 well plate; about 21.5 to about 22 mm, such as about 21.6 mm for a 12 well plate; and from about 34 to about 34.6 mm, such as about 34.2 mm for the 6 well plate.

Manufacture

The disclosure also encompasses methods of making the inserts described herein. The methods include providing a suitable polymer; and molding or 3D-printing the inserts using the polymer. If the inserts are molded, a softened or liquid polymer may be placed in a mold, allowed to harder or set, and then be removed from the mold. The disclosed inserts are generally manufactured (molded) or 3D printed as a single piece using an inert polymeric material. The polymeric material is robust, inflexible, does not absorb water, does not leach chemicals into the media and is stable at temperatures needed for cell culture, and optionally for sterilization. The inserts may be designed as single use inserts that are disposed after use, or as reusable inserts that withstand cleaning, sterilization and reuse. Examples of suitable polymeric materials for making the inserts include but are not limited to: acrylonitrile butadiene styrene (ABS), polycarbonate, polyphenylsulfone (PPSU, PPSF), polyethylene, ultra-high-molecular-weight polyethylene (UHM-WPE, UHMW), Glycol Modified Polyethylene Terephthalate (PETG), polystyrene (PS), Polypropylene (PP), polymethyl methacrylate (PMMA), Cycloolefin, etc.

In some aspects, the inserts are produced as single inserts which are placed, one at a time, into a well. Alternatively, a plurality of inserts may be connected (hooked together) in a strip or network or inserts. Strips and networks are designed to be inserted e.g. into an entire row of wells of a multiwell plate at one time, or into all wells of a multiwall plate.

Products that may be manufactured for sale using the inserts disclosed herein include but are not limited to: packages of single inserts, usually sold as packets containing multiple inserts, such as enough to fill all wells of a multiwell plate or multiple multiwell plates; or packages of strips, also usually containing enough strips to fill all rows of a multiwell plate or multiple multiwell plates; or networks designed to fill all wells of a multiwell plate, sold in packets to fill one or a plurality of multiple multiwell plates. Alternatively, the inserts may be sold in any of these forms (singly, strips, networks) together with multiwell plates for which they are adapted, as a single product or system. In addition, when the inserts and plates are sold as single, multipart product, substrates for use in the wells may be included. The inserts and/or substrates may be preinserted into the well of the plates, or packaged separately within the multipart product to be inserted by the end user.

Methods

Provided herein are methods of culturing cells so as to create or simulate an artificial wound in the cultured cells. The methods involve placing an insert as described herein into a cell culture well, or providing a cell culture well in which an insert as described herein has been placed (a cell culture well comprising an insert); introducing cells to be cultured into the well via one or more channels in the insert; incubating the cells under conditions that permit growth of the cells, wherein the cells cannot enter and grow in the section of the well that is blocked by the shaft of the insert; and removing the insert to expose the gap or "wound" in the cultured cells. In some aspects, a scaffold is provided at the bottom of the well, and the cells grow on and/or in the scaffold. In further aspects, a ring is provided that is insertable into the well, and which rests on top of the scaffold and serves to sequester or stabilize the position of the scaffold.

Also provided are methods of selecting compounds suitable for use in wound healing by screening candidate compounds using the cell cultures grown as described herein. The methods involve placing an insert as described herein into a cell culture well, or providing a cell culture well in which an insert as described herein has been placed (a cell culture well comprising an insert); introducing cells to be cultured into the well via the channels in the insert; incubating the cells under conditions that permit growth of the cells, wherein the cells cannot enter and grow in the section of the well (and/or the section of a scaffold that is present in the well) that is blocked by the shaft of the insert; removing the insert to expose the gap or "wound" in the cultured cells, the gap having been created by the shaft of the insert which blocked cell growth in the gap; contacting cultured cells with a candidate agent; and detecting the impact or effect of the candidate agent on the behavior of the cells as they "heal" the "wound" by migrating into the gap, compared to control cells which are not contacted by the candidate agent. If the effect of the candidate compound is a desired or positive effect, then the candidate compound is selected as a compound suitable for use in wound healing.

The wound healing assays typically use cells derived from either cell lines or primary isolations from blood or tissue. Cell culture conditions for various cell lines are known and readily available to those of skill in the art e.g. see the website located at attc.org. For cells derived from primary isolations, protocols are often developed in individual laboratories. Examples of types of cells that can be cultured using the cell culture system described herein include but are not limited to: fibroblasts, endothelial cells, epithelial cells, cancer cells of different tissue types (skin, ovary, breast, prostate, bone, intestinal, liver, kidney, prostate, etc.) and stem cells (embryonic stem cell, induced pluripotent stem cell, umbilical cord, umbilical cord-blood, placental, fetal and adult tissue specific mesenchymal stem cells), etc.

Types of candidate agents that can be tested using the cell culture systems include but are not limited to: chemical compounds (such as antimicrobial, anticancer, antioxidant and antiinflamatory compounds, cell cycle inhibitors, small molecules, monoclonal antibodies, cytokines and growth factors, etc.; nucleic acid constructs such as RNAi, mRNA, siRNA, shRNA, or vectors comprising or encoding these nucleic acids; proteins or recombinant proteins such as adenoviral, virus like particles, retroviral, herpes simplex viral; lipids such as fatty acids (stearic acid, palmitic acid, omega 3 fatty acid, etc.), oils, vitamins (A, D, E, K); saccharides such as glucose, fructose, lactose, glucosamine, dextrins, cellulose, chitin; nanomaterials, such as metal oxides and peroxides, carbon allotropes, minerals; etc, and combinations of these. In addition, various conditions may be tested which impact wound healing, e.g. pH; exposure to gases such as $O_2$; etc.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

We claim:

1. An insert to prevent cell growth in a predetermined area of a cell culture well, comprising
    i) a cover portion comprising
        a top surface and a bottom surface, wherein the cover portion extends between the top surface and the bottom surface, and comprises a flanged top section and a cylindrical bottom section contiguous with the flanged top portion; and
        at least one channel extending completely through the cover portion and opening at both the top surface and the bottom surface; and
    ii) a shaft portion having sides that extend from the bottom surface to a shaft bottom surface that is substantially planar;
    wherein the shaft portion has a cross-sectional area that is less than a cross-sectional area of the cylindrical bottom section, and wherein the shaft bottom surface rests against
    i) the bottom of the cell culture well or,
    ii) on a coating or substrate that has been pre-applied to the bottom of the cell culture well.

2. The insert of claim 1, wherein the cover portion and the shaft portion are molded as a single piece.

3. The insert of claim 1, wherein the insert is sized for use in a 96 well culture plate, a 48 well culture plate, a 24 well culture plate, a 12 well culture plate or a 6 well culture plate.

4. The insert of claim 1, wherein a shape of the shaft bottom surface is circular, ovoid, rectangular, linear or irregular.

5. The insert of claim 1, wherein the shaft portion is substantially cylindrical.

6. The insert of claim 1, wherein the shaft and/or shaft bottom surface is not circular.

7. The insert of claim 1, wherein the shaft and/or shaft bottom surface is substantially rectangular.

8. The insert of claim 1, wherein the shaft and/or shaft bottom surface is irregular in shape.

9. The insert of claim 1, wherein portions of the shaft and/or shaft bottom surface are linear in shape.

10. A method of creating an artificial wound in cells in culture, comprising
    securing a scaffold material against a bottom surface of a cell culture well by placing the insert of claim 1 into the cell culture well, wherein the shaft bottom surface of the shaft contacts the scaffold material and holds the scaffold material against a bottom surface of the cell culture well,
    introducing cells and culture medium into the cell culture well via the one or more channels in the top portion of the insert, and
    incubating the cells under conditions that permit cell growth on the scaffold material;
    wherein cells grow in a non-occluded area of the scaffold material that is not contacted by the shaft bottom surface, and cells do not grow in an occluded area of the scaffold material that is contacted by the shaft bottom surface, and wherein the occluded area forms an artificial wound.

11. The method of claim 10, wherein the scaffold material comprises a polymer.

12. The method of claim 10, wherein the scaffold material comprises one or more agents that affect or may affect wound healing.

13. A method of testing at least one agent for its ability to facilitate wound healing, comprising,
    creating an artificial wound in cultured cells by the method of claim 10,
    removing the insert from the cell culture well;
    incubating the cultured cells under conditions that permit cell growth; and
    assessing growth of the cultured cells,
    wherein if the cultured cells grow into the artificial wound at a rate that is greater than that at which cells grow into a control artificial wound, then the at least one agent facilitates wound healing.

14. The method of claim 13, wherein the control artificial wound is established by incubating cells in a control cell culture well in the absence of the at least one agent.

15. The method of claim 13, wherein the step of assessing includes measuring one or more of cell migration, speed, persistence and polarity.

16. The method of claim 13, wherein the at least one agent is or is comprised in the scaffold material.

* * * * *